(12) United States Patent
Tomlin

(10) Patent No.: US 8,585,732 B2
(45) Date of Patent: Nov. 19, 2013

(54) RETRIEVAL DEVICE WITH SIDEWALL GRIPPERS

(75) Inventor: Damian Tomlin, Pembroke Pines, FL (US)

(73) Assignee: DePuy Synthes Products, LLC, Raynham, MA (US)

( * ) Notice: Subject to any disclaimer, the term of this patent is extended or adjusted under 35 U.S.C. 154(b) by 1629 days.

(21) Appl. No.: 11/424,037

(22) Filed: Jun. 14, 2006

(65) Prior Publication Data

US 2007/0293928 A1    Dec. 20, 2007

(51) Int. Cl.
    *A61M 29/00*     (2006.01)
    *A61F 11/00*     (2006.01)

(52) U.S. Cl.
    USPC ........................... 606/200; 606/108

(58) Field of Classification Search
    USPC .......... 606/108, 198, 200; 623/1.11; 604/106, 604/107, 109
    See application file for complete search history.

(56) References Cited

U.S. PATENT DOCUMENTS

| | | | |
|---|---|---|---|
| 3,574,381 A | 4/1971 | Ocheltree | |
| 4,390,599 A | 6/1983 | Broyles | |
| 4,728,217 A | 3/1988 | Fink | |
| 4,864,824 A | 9/1989 | Gabriel et al. | |
| 4,909,789 A | 3/1990 | Taguchi et al. | |
| 4,981,756 A | 1/1991 | Rhandhawa | |
| 5,011,482 A * | 4/1991 | Goode et al. ................ 606/1 |
| 5,037,427 A * | 8/1991 | Harada et al. ............ 606/108 |
| 5,061,914 A | 10/1991 | Busch et al. | |
| 5,062,847 A | 11/1991 | Barnes | |
| 5,082,359 A | 1/1992 | Kirkpatrick | |
| 5,108,407 A | 4/1992 | Geremia et al. | |
| 5,178,957 A | 1/1993 | Kolpe et al. | |
| 5,197,978 A | 3/1993 | Hess | |
| 5,217,484 A * | 6/1993 | Marks ............................ 606/200 |
| 5,288,230 A | 2/1994 | Nikutowski et al. | |
| 5,334,216 A | 8/1994 | Vidal et al. | |
| 5,360,397 A | 11/1994 | Pinchuk | |
| 5,403,700 A | 4/1995 | Heller et al. | |
| 5,543,019 A | 8/1996 | Lee et al. | |
| 5,549,615 A * | 8/1996 | Hocherl et al. ............ 606/108 |
| 5,607,463 A | 3/1997 | Schwartz et al. | |
| 5,609,608 A | 3/1997 | Bennett et al. | |

(Continued)

FOREIGN PATENT DOCUMENTS

| | | |
|---|---|---|
| EP | 084773 A1 | 12/1997 |
| EP | 0641224 B1 | 8/1998 |

(Continued)

OTHER PUBLICATIONS

Spine; Hellier, Hedman, Kostuik; Wear Studies for development of an intervertebral disc prosteses; Jun. 1992; US.

(Continued)

*Primary Examiner* — Katherine Dowe
*Assistant Examiner* — Jonathan Hollm
(74) *Attorney, Agent, or Firm* — Cook Alex Ltd.

(57) ABSTRACT

A foreign body retrieval system includes a pusher and a retrieval element connected to the distal end of the pusher. The retrieval element includes one or more gripping members that are movable between a retracted position and an extended position. In the extended position, the gripping members extend in a radial and outward direction from the retrieval element in order to snag and capture a foreign body.

17 Claims, 2 Drawing Sheets

(56) References Cited

U.S. PATENT DOCUMENTS

| | | | |
|---|---|---|---|
| 5,629,077 A | 5/1997 | Turnlund et al. | |
| 5,656,036 A | 8/1997 | Palmaz | |
| 5,669,977 A | 9/1997 | Shufflebotham et al. | |
| 5,681,575 A | 10/1997 | Burrell et al. | |
| 5,685,961 A | 11/1997 | Pourrezaei et al. | |
| 5,735,892 A | 4/1998 | Myers et al. | |
| 5,744,958 A | 4/1998 | Werne | |
| 5,753,251 A | 5/1998 | Burrell et al. | |
| 5,766,710 A | 6/1998 | Turnlund et al. | |
| 5,770,255 A | 6/1998 | Burrell et al. | |
| 5,783,130 A | 7/1998 | Bennett et al. | |
| 5,810,870 A | 9/1998 | Myers et al. | |
| 5,814,062 A * | 9/1998 | Sepetka et al. | 606/198 |
| 5,827,304 A | 10/1998 | Hart | |
| 5,843,289 A | 12/1998 | Lee et al. | |
| 5,861,035 A | 1/1999 | Griffith | |
| 5,891,128 A * | 4/1999 | Gia et al. | 606/1 |
| 5,902,317 A | 5/1999 | Kleshinski et al. | |
| 5,908,409 A | 6/1999 | Rinehart et al. | |
| 5,910,144 A * | 6/1999 | Hayashi | 606/108 |
| 5,925,038 A | 7/1999 | Panescu et al. | |
| 5,925,075 A | 7/1999 | Myers et al. | |
| 5,941,895 A | 8/1999 | Myler et al. | |
| 5,945,153 A | 8/1999 | Dearnaley | |
| 5,951,586 A | 9/1999 | Berg et al. | |
| 5,989,242 A | 11/1999 | Saadat et al. | |
| 6,017,553 A | 1/2000 | Burrell et al. | |
| 6,043,451 A | 3/2000 | Julien et al. | |
| 6,096,175 A | 8/2000 | Roth | |
| 6,174,329 B1 | 1/2001 | Callol et al. | |
| 6,187,016 B1 | 2/2001 | Hedges et al. | |
| 6,203,732 B1 | 3/2001 | Clubb et al. | |
| 6,238,686 B1 | 5/2001 | Burrell et al. | |
| 6,319,277 B1 | 11/2001 | Rudnick et al. | |
| 6,322,588 B1 | 11/2001 | Ogle et al. | |
| 6,325,824 B2 | 12/2001 | Limon | |
| 6,342,067 B1 | 1/2002 | Mathis et al. | |
| 6,358,256 B1 * | 3/2002 | Reinhardt | 606/108 |
| 6,371,469 B1 | 4/2002 | Gray | |
| 6,432,116 B1 | 8/2002 | Callister et al. | |
| 6,436,132 B1 | 8/2002 | Patel et al. | |
| 6,447,478 B1 | 9/2002 | Maynard | |
| 6,471,721 B1 | 10/2002 | Dang | |
| 6,478,773 B1 | 11/2002 | Gahndi et al. | |
| 6,508,825 B1 * | 1/2003 | Selmon et al. | 606/198 |
| 6,527,919 B1 | 3/2003 | Roth | |
| 6,533,905 B2 | 3/2003 | Johnson et al. | |
| 6,537,310 B1 | 3/2003 | Palmaz et al. | |
| 6,605,111 B2 | 8/2003 | Bose et al. | |
| 6,627,246 B2 | 9/2003 | Mehta et al. | |
| 6,645,243 B2 | 11/2003 | Vallana et al. | |
| 6,660,032 B2 | 12/2003 | Klumb et al. | |
| 6,666,882 B1 | 12/2003 | Bose et al. | |
| 6,692,504 B2 | 2/2004 | Kurz et al. | |
| 6,726,993 B2 | 4/2004 | Teer et al. | |
| 6,772,014 B2 * | 8/2004 | Coe et al. | 607/119 |
| 6,783,530 B1 | 8/2004 | Levy | |
| 6,786,920 B2 | 9/2004 | Shannon et al. | |
| 6,802,846 B2 | 10/2004 | Hauschild et al. | |
| 6,805,898 B1 | 10/2004 | Wu et al. | |
| 6,989,020 B2 * | 1/2006 | Jones et al. | 606/200 |
| 7,144,408 B2 * | 12/2006 | Keegan et al. | 606/200 |
| 2001/0020182 A1 | 9/2001 | Klumb et al. | |
| 2001/0039449 A1 | 11/2001 | Johnson et al. | |
| 2002/0032478 A1 | 3/2002 | Boekstegers et al. | |
| 2002/0038143 A1 | 3/2002 | McCrea et al. | |
| 2002/0111667 A1 | 8/2002 | Girton et al. | |
| 2002/0151958 A1 | 10/2002 | Chuter | |
| 2003/0004567 A1 | 1/2003 | Boyle et al. | |
| 2003/0066533 A1 | 4/2003 | Loy | |
| 2003/0212429 A1 * | 11/2003 | Keegan et al. | 606/200 |
| 2004/0098094 A1 | 5/2004 | Boyle et al. | |
| 2004/0106932 A1 * | 6/2004 | Diaz et al. | 606/108 |
| 2004/0143288 A1 | 7/2004 | Searle | |
| 2007/0203518 A1 * | 8/2007 | Jones et al. | 606/200 |

FOREIGN PATENT DOCUMENTS

| | | |
|---|---|---|
| EP | 0824900 B1 | 4/2003 |
| EP | 1 099 004 B1 | 9/2004 |
| GB | 2331998 A | 6/1999 |
| WO | WO 93/07924 | 4/1993 |
| WO | 9323092 A1 | 11/1993 |
| WO | 9425637 A1 | 11/1994 |
| WO | WO 95/13704 | 5/1995 |
| WO | WO 97/26026 | 7/1997 |
| WO | WO 99/66966 | 12/1999 |
| WO | 0004204 A1 | 1/2000 |
| WO | WO 00 04204 | 1/2000 |

OTHER PUBLICATIONS

Biomaterials; Li; Behaviour of titanium and titania-based ceramics in vitro and in vivo; Feb. 2003; US.

Elsevier; Banks et al.; Ion bombardment modification of surfaces in biomedical applications; 399-434; 1984; Netherlands.

Advances in Bioengineering; Chung, Chang, Han; Development of thin metal film deposition process for the intravascular catheter; Conference; Nov. 14, 1999; US.

Journal of Materials Processing Technology; Kola, Daniels, Cameron, Hashmi; Magnetron suputtering of TiN protective coatings for medical applications; 422-430; Jan. 1996; Ireland.

Journal of Biomedical Materials Research; Yuhta et al.; Blood compatibility of stutter-deposited alumina films; 271-224; Feb. 1994.

Society for Biomaterials; Ong, Lucas, Lacefield, Rigney; Properties of calcium-phosphate coatings produced by ion-beam sputter deposition; Conference; May 1, 1991; US.

Asaio; Zabetakis, Cotell, Chrisey, Auyeung; Pulsed laser deposition of thin film hydroxyapatite. Applications for flexible catheters; 896-899; Jul. 1994; US.

* cited by examiner

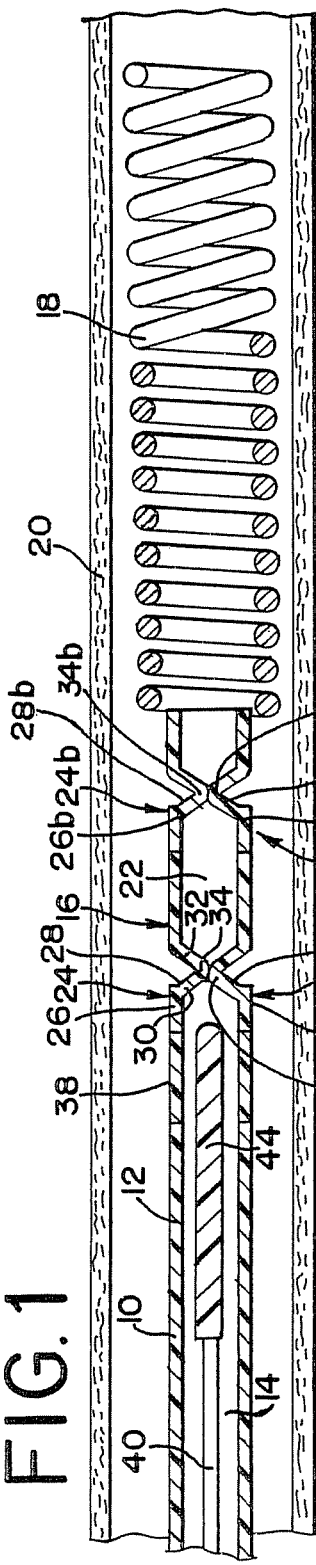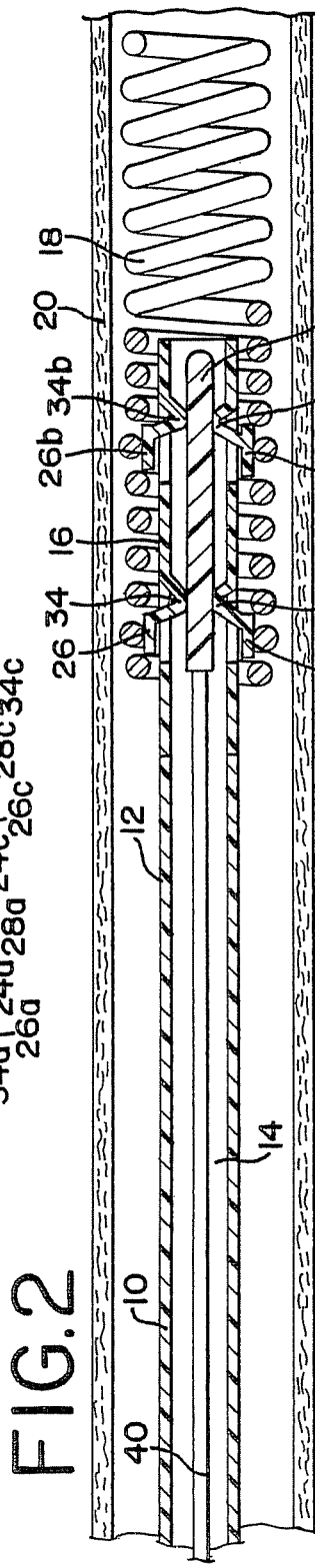

RETRIEVAL DEVICE WITH SIDEWALL GRIPPERS

FIELD OF THE INVENTION

This invention generally relates to devices and methods which are used to retrieve foreign objects from a patient, and more particularly to devices and methods which are employed to remove embolic coils or other implanted devices from blood vessels.

BACKGROUND OF THE INVENTION

Many surgical procedures have been developed for removing foreign objects from the body, particularly in the field of implantable objects. Implantable objects, such as embolic coils and stents, may require removal from the body for many different reasons. For example, an implant could be located at an undesired and potentially dangerous location, the patient's body could reject the implant or the implant may only be temporary and is required to be removed after a prescribed period of time.

One example of a situation wherein an implant is required to be removed from a patient is when an embolic coil is located at an undesired location within the vasculature of a patient. It is becoming a more common practice to treat aneurysms, particularly intercranial aneurysms, with embolic coils that are delivered to the aneurysm site with the aid of a microcatheter deployment system. While complications associated with embolic coil treatments are rare, occasionally, an embolic coil is deployed to the wrong location within the vascular of the patient or an implanted embolic coil becomes dislodged after implantation. In either scenario, the embolic coil may be free to flow through the vasculature and become lodged or implanted at an undesired location. In addition to being implanted at an undesired location, there is a chance that the misplaced embolic coil will lead to the formation of an unwanted occlusion, such as a thrombus or blood clot, which can cause serious health problems that may be life threatening.

When an embolic coil becomes misplaced within the vasculature of a patient, a procedure is performed to remove the embolic coil from the body. Depending on the location of the misplaced embolic coil, time can become a critical factor in the amount of damage caused by the misplaced embolic coil Thus, procedures for removing misplaced embolic coils should be preformed in a quick and efficient manner.

There remains a need that is recognized and addressed according to the present invention for a retrieval device which provides for a convenient and time efficient removal of foreign objects from the body.

SUMMARY OF INVENTION

The present invention generally relates to retrieval systems and methods employed to remove foreign objects, such as embolic coils and stents, from the human body. In one preferred embodiment, the retrieval system includes an elongated pusher having a proximal end portion and a distal end portion. A retrieval element is located at the distal end portion of the pusher. The retrieval element includes one or more gripping members that have a retracted position and an expanded position. In the retracted position, the gripping members are preferably generally flush with the outer surface of the retrieval element or below or slightly above the outer surface of the retrieval element. The expanded position is presented when a pushrod of the elongated pusher engages an internal surface of the gripping member in order to extend the gripping member in a lateral and outward direction from the retrieval device to engage and capture, preferably by snagging, the object to be retrieved, typically in a sidewall engaging fashion.

The pushrod is slidably located within the pusher and is movable between a first position and a second position. The pushrod includes an engagement portion or cam that contacts the internal surface of the gripping member when the pushrod is moved from the first position to the second position. When the cam contacts the gripping member internal surface, the latter functions in the nature of a cam follower as the cam imparts a force against the internal surface, which causes the gripping members to move into the extended position. In one embodiment, when the pushrod is moved back into the first position, the cam element disengages the gripping member internal surface, and biasing action of the gripping member assists in moving same back to the retracted position.

In a procedure to remove an embolic coil from the vasculature of a patient, the distal end of a guide catheter is placed at the site of an embolic coil to be removed, using other devices and professional procedures generally known in the art. The pusher is employed to guide the retrieval element having the gripping members in the retracted position through the guide catheter and out of the distal end portion of the guide catheter. The retrieval element may exit the guide catheter by either advancing the pusher or retracting the guide catheter, or both. The retrieval element is then inserted into the embolic coil, which can be of a variety of shapes including helically shaped or complex-shaped.

Once the retrieval element is in the desired position within the embolic coil, the pushrod is moved from the first position to the second position to move the gripping members into the extended position so that the gripping members engage and snag the embolic coil. The pusher is then retracted and/or the guide catheter is advanced to draw the retrieval element and embolic device into the guide catheter. The pusher is then retracted out of the guiding catheter or both the guiding catheter and the pusher are retracted out of the patient to remove the embolic coil.

It is an object or aspect of the present invention to provide devices and methods that allow the removal of a foreign body from a patient in a time efficient manner.

Another aspect or object of this invention is to provide devices and methods that extend a snaring component radially beyond a retrieval device external surface that enters a foreign body to be removed from a patient.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is a longitudinal partial cross-sectional view of a retrieval system in accordance with the present invention, shown within a blood vessel and with the gripping members in the retracted position;

FIG. 2 is a longitudinal partial cross-sectional view of the retrieval system of FIG. 1, shown with the gripping members in the expanded position to engage an embolic coil;

FIG. 3 is an enlarged perspective view of the retrieval element of the retrieval system of FIG. 1;

DESCRIPTION OF THE PREFERRED EMBODIMENTS

Figure 4:
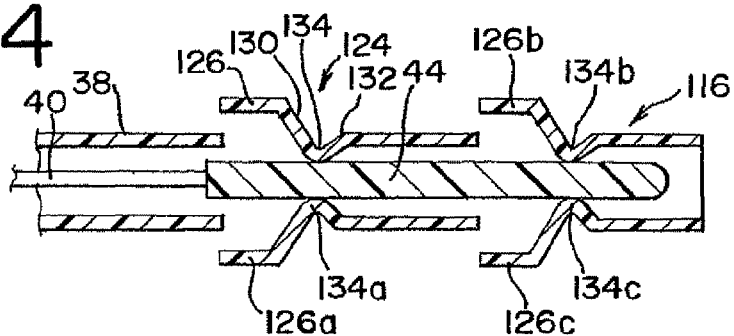
FIG. 4 is a partial cross-sectional view of another embodiment of the retrieval element of the present invention, shown with the gripping members in the extended position.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Further, the retrieval system of the present invention is designed for removing foreign bodies from within a patient. However, for the sake of convenience, the description of the retrieval device herein will be described in terms of retrieving and removing an embolic coil from the vasculature of a patient. It will be understood that the description herein does not limit the present invention to only such uses.

FIGS. 1 and 2 illustrate an embodiment of the retrieval system of the present invention. The retrieval system includes an elongated flexible pusher 10 which has a proximal end portion (not shown), a distal end portion 12 and a lumen 14 extending therethough. A retrieval element 16 is located at the distal end portion 12 of the pusher 10, and the pusher 10 is manipulated in order to guide the retrieval element 16 to the site of a foreign body, such as an embolic coil 18 within a blood vessel 20. The embolic coil could have a helical shape or a complex shape. The pusher 10 should have sufficient flexibility and column strength to traverse the vasculature of the patient.

Referring to FIGS. 1 and 3, the retrieval element 16 can be a tubular shaped structure with a lumen 22 extending therethough. The retrieval element 16 includes a plurality of gripping members, generally designated as 24, 24a, 24b and 24c, that have a retracted position (shown in FIGS. 1, 3, 5 and 7) and an extended position (shown in FIGS. 2, 4 and 6). As shown, the retrieval element 16 includes four gripping members; however, the number of gripping members can vary depending on the desired treatment. The gripping members 24, 24a, 24b and 24c include a gripper or button 26, 26a, 26b and 26c and an extender element 28, 28a, 28b and 28c.

The gripping members 24, 24a, 24b, and 24c will generally be described with reference to gripping member 24. In the illustrated embodiment, the extender element 28 comprises a first arm 30 and a second arm 32 with an elbow portion 34 therebetween. As discussed elsewhere herein, the elbow portion functions in the general nature of a cam follower to effect extending action of the gripping member.

In this illustrated embodiment, the first arm 30 is connected to the gripper 26, the second arm 32 is connected to the retrieval element 16 and the elbow portion 34 extends into the lumen 22 of the retrieval element 16 through an orifice 36, as perhaps best seen in FIG. 3. The gripping members 24, 24a, 24b and 24c are preferably arranged so that each gripping member is aligned with an opposed gripping member located on the opposite side of the retrieval element 16. For example, in the illustrated embodiment, gripping member 24 is opposite gripping member 24a, and gripping member 24b is opposite gripping member 24c. The gripping members are aligned in this fashion so that the elbow portions 34, 34a and 34b, 34c of each of the extender elements also are aligned.

In the retracted position, the gripper 26 is preferably generally flush with the outer surface 38 of the retrieval element 16, as illustrated in FIGS. 1, 3, 5 and 7. As shown, the gripper 26 resides in the orifice 36 and the extender element 28 extends into the lumen 22 of the retrieval element 16. It is contemplated that the gripper 26 could also reside above or below the outer surface 38 of the retrieval element.

Referring to FIGS. 1 and 2, a pushrod 40 is slidably located within the lumen 14 of the catheter and can be axially advanced and retracted into the lumen 22 of the retrieval element 16, as desired. The pushrod 40 includes an engagement end or cam 44 preferably located at the distal end portion of the pushrod. The pushrod 40 can be moved from a first position in which the cam 44 resides in the lumen 14 of the pusher 10 to a second position in which the cam is inserted into the lumen 22 of the retrieval element 16 so that the cam 44 is positioned between the opposed cam followers, which are illustrated as the elbow portions 34, 34a and 34b and 34c of the extender elements.

Figure 6:
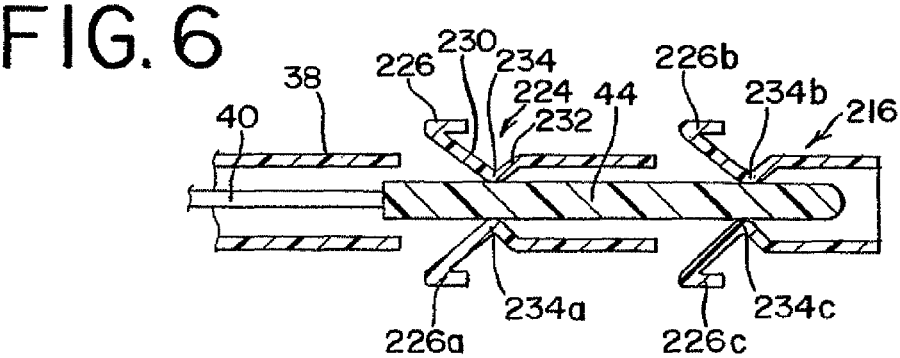
FIG. 6 is an enlarged cross-sectional view of yet another embodiment of the retrieval element of the present invention, shown with the gripping members in the extended position.

Inserting the cam portion 44 of the pushrod 40 between the elbow portions of the spring elements pushes opposing elbow portions apart, causing the grippers 26, 26a, 26b and 26c to extend in a lateral and outward direction from the retrieval element 16, as shown in FIGS. 2, 4 and 6. This can be considered as movement of sidewall grippers for retrieval.

When the pushrod 40 is moved back into the first position, the cam 44 is retracted from in between the cam followers or elbow portions 34, 34a, 34b and 34c, allowing the grippers to return to their retracted position as shown in FIGS. 1, 3, 5 and 7. This return can be facilitated and/or achieved by having the extender element 28 be biased toward the retracted position, such as having the extender operate as a spring element that returns to the retracted position when not prevented from doing so by another component. Alternatively, the gripping member 24 can be formed so that the gripper 26 stays in the extended position after the cam 44 has been retracted from engagement with the cam followers such as from in between opposing elbow portions.

The retrieval element 16 can have a variety of configurations without departing from the present disclosure. For instance, the retrieval element 16 can be attached to the distal end portion 12 of the pusher 10 by, for example, adhesive, soldering or any other suitable attachment method. Alternatively, the retrieval element 16 can be integral with the pusher 10.

Figure 8:
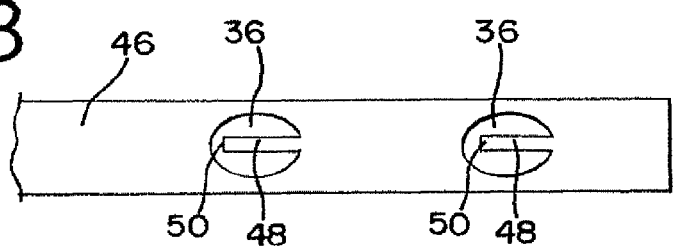
FIG. 8 is a top view of a hypotube from which a retrieval element can be made.

Further, the retrieval element 16 also can be formed in a variety of different ways. For example, the retrieval element can be created from a metal hypotube which is cutout, preferably by laser cutting, to form at least a portion of each gripping member. The embodiment of the retrieval element 16 illustrated in FIGS. 1, 2 and 3 can be created by cutting the sidewall of a hypotube 46 to form the orifice 36 with a remaining portion or strip 48 of the hypotube projecting partially across the orifice, as illustrated in FIG. 8. The strip 48 is then bent to form the first and second extension element arms 30, 32 and the intervening cam follower or elbow portion 34. After the arms have been formed, the gripper or button 26 is attached to the first extension element arm 30 by, for example, adhesive or solder.

Figure 5:
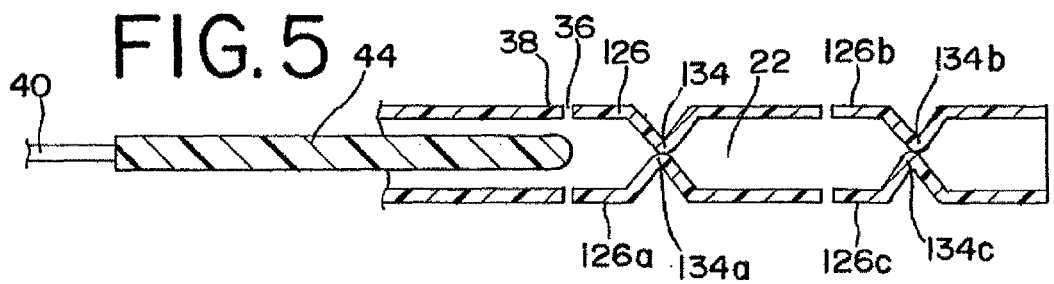
FIG. 5 is an enlarged cross-sectional view of the retrieval element of FIG. 4, shown with the gripping members in the retracted position.

In alternative embodiments, the hypotube can be cutout in the same manner as described above to make retrieval element 116, and the remaining strip can be bent to form the entirety of the gripping member 124. For example, in making a device as shown in FIGS. 4 and 5, the strip of hypotube projecting into the orifice made in the hypotube is bent to form the gripper 126, 126a, 126b and 126c and the first and second extension element arms 130, 132 of a gripping member 124. As illustrated, the free end portion 50 of the strip 48 is bent away from the first spring arm 130 to form the gripper 126. The gripping members are aligned in this fashion so that elbow portions 134, 134a and 134b, 134c between respective element arms 130, 132 also are aligned.

Figure 7:
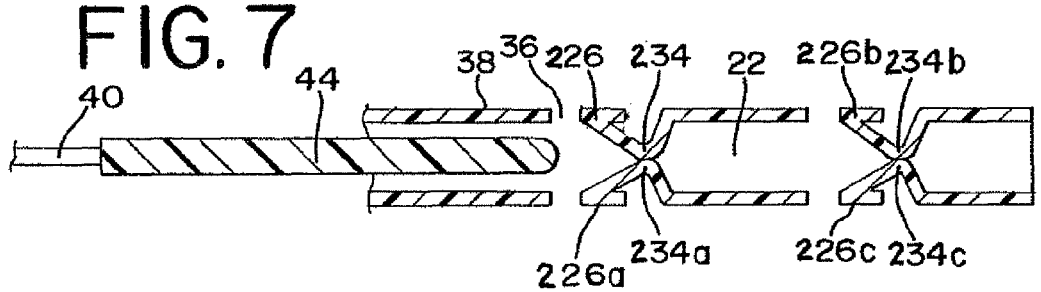
FIG. 7 is an enlarged cross-sectional view of the retrieval element of FIG. 6, shown with the gripping members in the retracted position.

In FIGS. 6 and 7, a further retrieval element 216 is illustrated. The gripping member 224 of this embodiment is formed in the same manner just described, except that the free end portion of the strip formed within the orifice that is formed in the hypotube is folded back over the first arm 230 to form the gripper 226, 226a, 226b and 226c, making an integral hook-like gripping member 224 from the strip cut out from the hypotube. Each gripping member 224 includes an elbow portion 234, 234a, 234b, 234c between the first arm 230 and a second arm 232.

The retrieval element can be constructed of a variety of materials. For example, the retrieval element can be made of a metal, such as stainless steel, a shape memory alloy, such as a Nitinol alloy, or a suitable biocompatible polymer. When the retrieval element is to have spring-like or biasing properties, it can be made from a hypotube comprised of a shape memory material such as a Nitinol alloy. Such a shape memory material can be heat set so that the gripping members are in the retracted position at human body temperature. Because of the characteristics of the shape memory material in these circumstances, the shape memory material returns to its heat set shape after deformation. Thus, the shape memory characteristic causes the gripping members to have a greater tendency to return to the retracted position after the cam has been removed from engagement with the cam followers, such as from in between opposing elbow portions of the gripping members.

FIGS. 1 and 2 illustrate the retrieval of an embolic coil 18 from a blood vessel 20. This illustration is in no way meant to limit the present invention to only such uses. It is useful where an extending member can directly engage a member deployed within a body lumen, it being especially advantageous for use within very narrow body passageways.

In a typical operational use, a guide catheter (not shown) is inserted into the vasculature of a patient and positioned at a location adjacent the embolic coil 18 to be removed, typically in conjunction with other devices and professional procedures as generally known in the art. The pusher 10 of the retrieval system is advanced through the guide catheter to place the retrieval element 16 at the distal end of the guide catheter. Once the retrieval element 16 has reached the distal end of the guide catheter, the pusher 10 is advanced and/or the guide catheter is moved in retrograde fashion until the retrieval element 16 has exited the distal end portion of the guide catheter.

The pusher 10 then is used to insert the retrieval element 16 into the embolic coil 18. Once the retrieval element 16 is in the desired position, the pushrod 40 is advanced distally so that the cam 44 is inserted between the cam followers, such as the elbow portions 34, 34a and 34b, 34c of the extension elements. Insertion of the cam 44 between the elbow portions 34, 34a and 34b, 34c of the extension elements causes the grippers 26, 26a, 26b, 26c to move into the expanded position, snagging the embolic coil 18, as shown in FIG. 2.

The pusher 10 may then be used to retract the retrieval element 16 and the snagged embolic coil 18 into the guide catheter. Removal of the guide catheter with the guide catheter secured to same allows full removal of the embolic coil out of the patient. It will be understood that the present invention may be used in conjunction with other medical procedures and devices. This includes removal of devices other than embolic coils.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A retrieval system for retrieving an embolic coil having a plurality of generally circumferential windings from a patient, comprising:
    an elongated flexible, non-expandable pusher having a proximal end portion, a distal end portion and a lumen extending therethrough;
    a retrieval element located at the distal end portion of the pusher, the retrieval element being made from a hypotube and including at least one orifice with a gripping member therewithin which is movable between a retracted position and an extended position, the gripping member projecting in a radial and outward direction from the at least one orifice of the retrieval element when the gripping member is in the extended position;
    said gripping member has a free end and a connected end that is connected to the retrieval element at the orifice, and a gripper at the free end;
    said gripping member is generally V-shaped, said gripping member having a first arm having the gripper, a second arm and a single elbow therebetween, said gripper having an axially oriented surface spaced radially outwardly from said elbow;
    said gripping member first arm is oriented radially inwardly in a direction away from the gripper at the free end and toward the elbow, said elbow connects the first arm to the second arm, said second arm is oriented radially outwardly in a direction away from the elbow, said second arm comprising the connected end and being connected to the retrieval element through a living hinge connection at a selected location along the orifice and only at said selected location, said gripping member being movable to cause the gripping member to move into the extended position;
    the hypotube retrieval element and the gripping member, which includes, in order, the living hinge connection, second arm, elbow, first arm, gripper and axially oriented surface at the free end, are integral with each other in that the gripping member is made by cutting out and bending a portion of the hypotube;
    a pushrod slidably located within the lumen of the pusher, said pushrod being longitudinally movable between a first position and a second position; and
    wherein movement of said pushrod from the first position to the second position places the pushrod into contact with the elbow portion of the generally V-shaped gripping member to cause the second arm of the gripping to bend at the living hinge connection, whereby the gripping member moves into the extended position and the gripper axially oriented surface engages and moves a winding of the embolic coil to a location spaced radially outwardly from the elbow whereby the winding of the embolic coil is spaced radially outwardly from an adjacent winding thereby snagging the embolic coil.

2. The retrieval system of claim 1, wherein the gripping member is biased toward the retracted position of the gripper member.

3. The retrieval system of claim 2, wherein the pushrod disengages the gripping member when the pushrod moves from the second position to the first position,
   causing the biased extension element to move the gripping member toward the retracted position.

4. The retrieval system of claim 2, wherein the retrieval element is made of a shape memory material.

5. The retrieval system of claim 1, wherein the retrieval element is a separate component that is secured to the distal end portion of the pusher.

6. The retrieval system of claim 1, wherein the gripper is generally flush with an outer surface of the retrieval element and the elbow portion is positioned radially inwardly when the gripping member is in the retracted position.

7. The retrieval system of claim 1, wherein the retrieval element is tubularly shaped and includes a plurality of the gripping members, the gripping members being arranged so that the elbow portion of each gripping member is located at a position that is opposite the elbow portion of another gripping member along the retrieval element.

8. The retrieval system of claim 7, wherein the opposing elbow portions engage each other when the gripping member is in the retracted position.

9. The retrieval system of claim 1, wherein said gripping member axially oriented surface is a surface folded over from the first arm.

10. A retrieval system for retrieving an embolic coil having a plurality of generally circumferential windings from a patient, comprising:
   an elongated flexible pusher having a proximal end portion, a distal end portion and a lumen extending therethrough;
   a retrieval element being made from a hypotube and located at the distal end portion of the pusher, the retrieval element including a plurality of orifices, each with a gripping member therein, each gripping member being movable between a retracted position and an extended position, each gripping member projecting in a radial and outward direction from the retrieval element when each gripping member is in the extended position;
   each gripping member having a free end and a connected end that is connected to the retrieval element at the orifice, and a gripper at the free end;
   each gripping member being biased and generally V-shaped biasing the gripping member toward the retracted position, each said gripping member having a first arm having the gripper, a second arm and a single elbow therebetween, said gripper having an axially oriented surface spaced radially outwardly from said elbow;
   each said gripping member first arm is oriented radially inwardly in a direction away from the gripper at the free end and toward the elbow, said elbow connects the first arm to the second arm, said second arm is oriented radially outwardly in a direction away from the elbow, said second arm comprising the connected end and being connected to the retrieval element through a living hinge connection at a selected location along a respective orifice and only at said selected location, each said gripping member being movable to cause the gripping member to move into the extended position;
   the hypotube retrieval element and the gripping member, which includes, in order, the living hinge connection, second arm, elbow, first arm, gripper and axially oriented surface at the free end, are integral with each other in that the gripping member is made by cutting out and bending a portion of the hypotube;
   a pushrod slidably located within the lumen of the pusher, said pushrod being longitudinally movable between a first position and a second position; and
   wherein movement of said pushrod from the first position to the second position contacts the pushrod with the elbow portion of each said generally V-shaped spring-biased extension element to cause the second arm of the gripping member to bend at the living hinge connection, whereby the plurality of gripping members move into the extended position, and wherein each axially oriented surface engages and moves a winding of the embolic coil to a location spaced radially outwardly from the elbow whereby the winding of the embolic coil is spaced radially outwardly from an adjacent winding thereby snagging the embolic coil.

11. The retrieval system of claim 10, wherein the pushrod disengages the biased gripping member when the pushrod moves from the second position to the first position, causing the gripping member to move back toward the retracted position.

12. The retrieval system of claim 10, wherein said each gripping member axially oriented surface is a surface folded over from the first arm.

13. A method for retrieving an embolic coil having a plurality of generally circumferential windings from a vessel within a patient, comprising:
   providing a retrieval system comprising an elongated flexible, non-expandable pusher having a retrieval element, the retrieval element being made from a hypotube and including at least one orifice with a gripping member capable of moving between a retracted position and an expanded position;
   providing the gripping member so as to have a free end and a connected end that is connected to the retrieval element at the at least one orifice and a gripper at the free end, each gripping member being generally V-shaped including a first arm and a second arm with a single elbow therebetween such that the first arm is oriented radially inwardly away from the free end and toward the elbow, the elbow connects the first arm and the second arm, the second arm is oriented radially outwardly in a direction away from the elbow, and the second arm comprising the connected end and being connected to the retrieval element through a living hinge connection at a selected location along the orifice and only at this selected location, wherein in the expanded position the gripping member extends in a radial and outward direction from the retrieval element;
   the gripping member being integrally formed by cutting and bending the retrieval element hypotube into the gripping member including, in order, the living hinge connection, second arm, elbow, first arm, and a gripper axially oriented surface at the free end spaced radially from the elbow;
   manipulating the pusher to place the retrieval element adjacent an embolic coil located in a vessel of the body;
   inserting the retrieval element into the embolic coil;

moving the gripping member from the retracted position to the extended position at which the gripper extends radially and outwardly beyond the orifice and the retrieval element including bending the second arm at the living hinge connection to engage and move a winding of the embolic coil to a location spaced radially outwardly from the elbow and from an adjacent winding of the embolic coil thereby snagging the embolic coil; and removing the retrieval element and the snagged embolic coil from the vessel.

14. The method according to claim 13, wherein manipulating the pusher comprises guiding the pusher through a guide catheter to place the retrieval element adjacent the embolic coil.

15. The method according to claim 13, wherein the gripping member biases the gripping member to the retracted position, said gripping member being movable to cause the gripping member to move into the extended position;

the pusher including a pushrod slidably movable within the pusher, the pushrod being movable between a first position and a second position wherein movement of the pushrod from the first position to the second position contacts the pushrod and the gripping member to cause the gripping member to move into the extended position; and moving the gripping member from the retracted position to the extended position comprises moving the pushrod from the first position to the second position so that said pushrod contacts a spring element to cause the gripping member to move into the extended position.

16. The method according to claim 15, wherein said moving of the gripping member includes camming action between a cam surface of the pushrod and a cam follower surface of the gripping member, said camming action effecting outwardly directed radial movement of the gripping member into engagement with the embolic coil.

17. The method according to claim 13, wherein providing the gripper member includes bending the first arm to form the axially oriented surface.

* * * * *